(12) United States Patent
Urman et al.

(10) Patent No.: US 10,980,439 B2
(45) Date of Patent: Apr. 20, 2021

(54) WAVEFRONT ANALYSIS BASED ON ABLATION PARAMETERS

(71) Applicant: BIOSENSE WEBSTER (ISRAEL) LTD., Yokneam (IL)

(72) Inventors: Roy Urman, Karkur (IL); Shmuel Auerbach, Kerem Maharal (IL); Yaniv Ben Zriham, Binyamina (IL); Assaf Pressman, Pardes Hanna-Karkur (IL); Eliahu Zino, Atlit (IL)

(73) Assignee: BIOSENSE WEBSTER (ISRAEL) LTD, Yokeam (IL)

( * ) Notice: Subject to any disclaimer, the term of this patent is extended or adjusted under 35 U.S.C. 154(b) by 280 days.

(21) Appl. No.: 14/452,675

(22) Filed: Aug. 6, 2014

(65) Prior Publication Data
US 2016/0038047 A1    Feb. 11, 2016

(51) Int. Cl.
*A61B 5/042* (2006.01)
*A61B 5/00* (2006.01)
(Continued)

(52) U.S. Cl.
CPC ............ *A61B 5/042* (2013.01); *A61B 5/0452* (2013.01); *A61B 5/055* (2013.01); *A61B 5/4848* (2013.01); *A61B 5/742* (2013.01); *A61B 5/743* (2013.01); *A61B 5/7485* (2013.01); *A61B 8/0883* (2013.01); *A61B 5/0422* (2013.01); *A61B 18/1492* (2013.01); *A61B 2017/00044* (2013.01); *A61B 2017/00053* (2013.01); *A61B 2018/00357* (2013.01); *A61B 2018/00666* (2013.01); *A61B 2018/00672* (2013.01);
(Continued)

(58) Field of Classification Search
CPC .. A61B 8/0883; A61B 5/4848; A61B 18/1492
See application file for complete search history.

(56) References Cited

U.S. PATENT DOCUMENTS 5,385,146 A * 1/1995 Goldreyer ............ A61B 5/0422
600/374
5,755,664 A    5/1998 Rubenstein
(Continued)

FOREIGN PATENT DOCUMENTS

JP    2007-038005    2/2007
JP    2013-233436    11/2013
(Continued)

OTHER PUBLICATIONS

EP15174477.8 Extended Search Report—dated Dec. 11, 2015.
(Continued)

*Primary Examiner* — Jason M Ip
(74) *Attorney, Agent, or Firm* — Louis J. Capezzuto (57) ABSTRACT

A method, including recording parameters indicative of a quality of ablation performed at one or more sites in a region of a human heart, and receiving a set of electrophysiological signals indicative of a wave of electrical activation flowing through the region. The method further includes identifying locations within the region at which the wave is blocked from flowing and estimating confidence levels with respect to a blockage of the wave at the locations in response to the signals and the parameters. The method also includes displaying a map of the human heart including an indication of the confidence levels.

15 Claims, 8 Drawing Sheets

(51) Int. Cl.
*A61B 18/00* (2006.01)
*A61B 18/14* (2006.01)
*A61B 5/0452* (2006.01)
*A61B 5/055* (2006.01)
*A61B 8/08* (2006.01)
*A61B 17/00* (2006.01)
*A61B 90/00* (2016.01)

(52) U.S. Cl.
CPC ............... *A61B 2018/00779* (2013.01); *A61B 2018/00791* (2013.01); *A61B 2018/00839* (2013.01); *A61B 2018/00886* (2013.01); *A61B 2090/064* (2016.02); *A61B 2090/374* (2016.02); *A61B 2090/378* (2016.02); *A61B 2505/05* (2013.01)

(56) References Cited

U.S. PATENT DOCUMENTS

| | | | |
|---|---|---|---|
| 7,245,962 B2 | 7/2007 | Ciaccio et al. | |
| 7,681,579 B2 | 3/2010 | Schwartz | |
| 8,457,721 B2 | 6/2013 | Desai | |
| 8,900,225 B2 | 12/2014 | Bar-Tal et al. | |
| 2004/0187875 A1* | 9/2004 | He | A61B 18/1492 128/898 |
| 2005/0203502 A1 | 9/2005 | Boveja et al. | |
| 2007/0299353 A1* | 12/2007 | Harlev | A61B 5/0422 600/509 |
| 2008/0219536 A1 | 9/2008 | Liao | |
| 2011/0082451 A1 | 4/2011 | Melsky | |
| 2012/0105480 A1* | 5/2012 | Barley | A61B 90/36 345/641 |
| 2012/0184863 A1 | 7/2012 | Harlev et al. | |
| 2012/0209260 A1 | 8/2012 | Lambert et al. | |
| 2012/0296232 A1* | 11/2012 | Ng | A61B 18/1492 600/554 |
| 2014/0022250 A1 | 1/2014 | Mansi et al. | |

FOREIGN PATENT DOCUMENTS

| | | | |
|---|---|---|---|
| WO | WO 2007/146864 A2 | 12/2007 | |
| WO | WO 2007146864 * | 12/2007 | ............... A61B 5/04 |
| WO | WO 2010/140069 A1 | 12/2010 | |
| WO | WO 2012/092016 A1 | 7/2012 | |
| WO | WO 2014/115148 A1 | 7/2014 | |

OTHER PUBLICATIONS

Axel Meissner et al., "Segmental Pulmonary Vein Isolation in atrial fibrillation: new insights from the high density mesh mapper technique in an electrophysiologically guide approach", Journal of Interventional Cardic Electrophysiology, Kluwer Academic Publishers, Bo, vol. 25, No. 3, 6 Mar. 2009, pp. 183-192.

Japanese Application No. 2015-154950—Examination Report dated May 28, 2019.

* cited by examiner

WAVEFRONT ANALYSIS BASED ON ABLATION PARAMETERS

FIELD OF THE INVENTION

The present invention relates generally to measurements of physical parameters associated with a body organ such as the heart, and specifically to analysis of an electrical wavefront progressing through the heart.

BACKGROUND OF THE INVENTION

Radiofrequency ablation is a well-known procedure in which part of the electrical conduction system of the heart is ablated using the heat generated from high frequency alternating current. The ablation is normally applied to correct atypical behavior of the heart, such as atrial fibrillation. The atypical behavior may be identified by acquiring electrophysiological signals from the heart, generating an electrical wavefront progressing through the heart from the signals, and comparing the wavefront generated with the electrical wavefront of a normal beating heart—one which is in sinus rhythm.

SUMMARY OF THE INVENTION

An embodiment of the present invention provides a method, including:

recording parameters indicative of a quality of ablation performed at one or more sites in a region of a human heart;

receiving a set of electrophysiological signals indicative of a wave of electrical activation flowing through the region;

identifying locations within the region at which the wave is blocked from flowing;

estimating confidence levels with respect to a blockage of the wave at the locations in response to the signals and the parameters; and displaying a map of the human heart including an indication of the confidence levels.

In a disclosed embodiment the parameters include one or more of a power applied during the ablation, a length of time of the ablation, a force magnitude on a probe applying the ablation, and a temperature of tissue undergoing the ablation. Typically, the method includes increasing the confidence levels as at least one of the power, the length of time, the force magnitude, and the temperature increases.

In a further disclosed embodiment the method includes increasing a given confidence level at a given location if an amplitude of a given electrophysiological signal at the given location is lower than the amplitude of the signal at the given location prior to the ablation.

In a yet further disclosed embodiment identifying the locations includes inspecting an electrophysiological surface map generated in response to the set of electrophysiological signals. Typically, the map is configured to provide an indication of a re-entrant arrhythmia.

In an alternative embodiment the parameters include an assessment of the quality of the ablation based on at least one of a magnetic resonance imaging (MRI) image and an ultrasound image of the one or more sites.

In a further disclosed embodiment displaying the map includes displaying a line illustrating a path wherein the wave is blocked from flowing, wherein the path is weighted by the confidence levels.

There is further provided, according to an embodiment of the present invention embodiment of the present invention, apparatus, including:

a screen; and a processor configured to:

record parameters indicative of a quality of ablation performed at one or more sites in a region of a human heart, receive a set of electrophysiological signals indicative of a wave of electrical activation flowing through the region, receive identified locations within the region at which the wave is blocked from flowing, estimate confidence levels with respect to a blockage of the wave at the locations in response to the signals and the parameters, and display a map of the human heart including an indication of the confidence levels on the screen.

In an embodiment, the apparatus includes a probe configured to acquire the set of electrophysiological signals and to convey the signals to the processor.

The present disclosure will be more fully understood from the following detailed description of the embodiments thereof, taken together with the drawings, in which:

DETAILED DESCRIPTION OF EMBODIMENTS

Overview

An embodiment of the present invention provides a method and a system for displaying the results of an ablation procedure on a region of a human heart, in order to evaluate the efficacy of the procedure. Typically, a map of the region incorporating cardiac electrophysiological data is initially presented to a user of the system. The data may be presented in the form of a three-dimensional (3D) map of local activation times (LATs) in the region, and is indicative of a wave of electrical activation flowing through the region. From the map, the user may identify areas within the region at which the wave appears to be blocked from flowing.

Within or in proximity to the identified areas, the user typically selects sites that are to be ablated, and then ablates the selected sites. For each ablated site, a processor of the system records parameters indicative of a quality of the ablation performed. The parameters typically include variables such as a power applied during the ablation, a length of time of the ablation, and a force applied, to tissue being ablated, by a probe performing the ablation.

After the sites have been ablated, a further set of electrophysiological signals may be acquired in order to evaluate the ablations performed. From the further set a map may be prepared displaying the updated electrophysiological data, e.g., as updated LATs. The map may display locations of the sites ablated. Optionally, the map may display a confidence level for each of the sites, the confidence level being estimated according to the recorded ablation parameters for the ablated sites, as well as according to the further set of electrophysiological signals in the region of the sites. Further optionally, the map may display a line indicating where the electrical activation wave is blocked, the path followed by the line being based on the confidence levels.

Displaying confidence levels and/or entities based on the confidence levels, such as the line referred to above, acts as an aid to the user of the system in evaluating the effectiveness of the ablation procedure performed.

System Description

Figure 1:
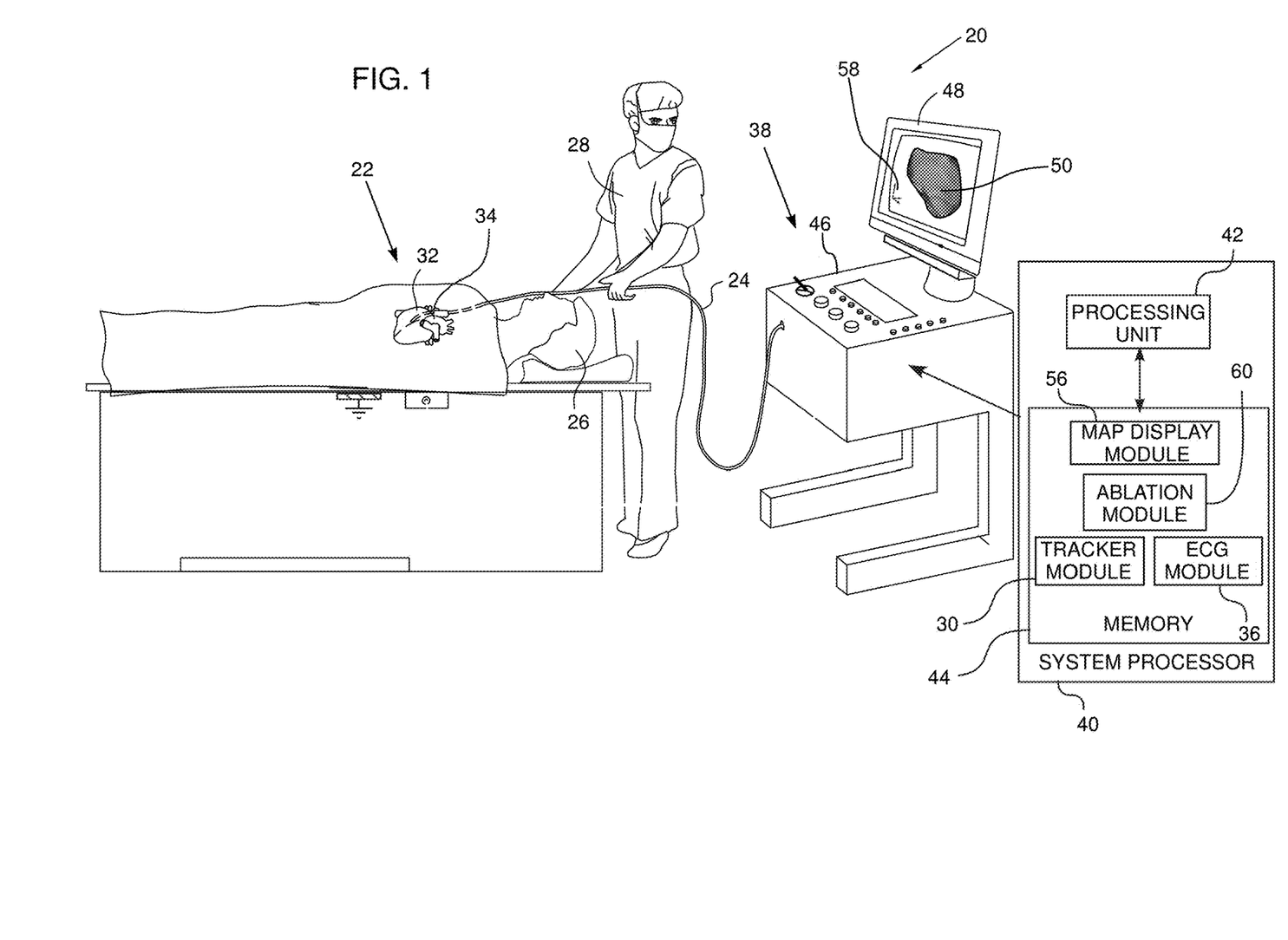
FIG. 1 is a schematic illustration of a wavefront blockage identification system, according to an embodiment of the present invention.

Reference is now made to FIG. 1, which is a schematic illustration of a wavefront blockage identification system 20, according to an embodiment of the present invention. In one embodiment system 20 is used to identify blockages in the progression of an electrical wavefront in a human organ, and in order to identify the blockages, the system, inter alia, maps electropotentials that are associated with the wavefront. For simplicity and clarity, the following description, except where otherwise stated, assumes an investigative procedure wherein system 20 senses electropotentials from electrical signals generated by a body organ 34, herein assumed to comprise a heart, using a probe 24.

In some embodiments, the sensed electropotentials may be used to derive local activation times (LATs) of the tissue generating the electropotentials, and system 20 may be configured to map the LATs. The measurement of LATs from their associated potentials is well known in the electrophysiological arts. However, system 20 may be configured to derive and map substantially any electropotential parameter or combinations of such parameters for any human organ, and the system is not limited to LATs.

A distal end 32 of probe 24 is assumed to have an electrode 22 attached to the distal end for acquiring the electrical signals processed by system 20. Those having ordinary skill in the art will be able to adapt the description for multiple probes that may have one or more electrodes, or for a single probe with multiple electrodes, as well as for signals produced by organs other than a heart.

Typically, probe 24 comprises a catheter which is inserted into the body of a human subject 26 during a mapping procedure performed by a user 28 of system 20. In the description herein user 28 is assumed, by way of example, to be a medical professional.

System 20 may be controlled by a system processor 40, comprising a processing unit 42 communicating with a memory 44. Processor 40 is typically mounted in a console 46, which comprises operating controls 38 that professional 28 uses to interact with the processor. Results of the operations performed by processor 40 are provided to the professional on a screen 48 which displays a three-dimensional (3D) electrophysiological map 50 of heart 34. Map 50 is herein also termed resultant map 50, to distinguish it from intermediate maps or meshes, described in more detail below, that processor 40 may use in generating map 50. Resultant map 50 illustrates values of the electropotential parameters, e.g., LATs in the example described herein, of heart 34 drawn with respect to a frame of reference 58. In addition, as is also described below, resultant map 50 displays locations of wavefront blockages, and indications of a confidence level assigned to each of the blockages.

The screen typically displays other items of auxiliary information related to the heart and superimposed on the map, while the heart is being investigated, such as the positions of catheters used by professional 28.

Using controls 38, professional 28 is able to vary parameters of the frame of reference, so as to display the resultant map in a selected orientation and/or at a selected magnification on screen 48. Screen 48 typically also presents a graphic user interface to the user, and/or a visual representation of the ECG signals sensed by electrode 22.

Processor 40 uses software, including an ECG module 36, a probe tracker module 30, an ablation module 60 and a map display module 56, stored in memory 44, to operate system 20. The functions of the modules are described below. The software may be downloaded to processor 40 in electronic form, over a network, for example, or it may, alternatively or additionally, be provided and/or stored on non-transitory tangible media, such as magnetic, optical, or electronic memory.

ECG module 36 is coupled to receive electropotential signals from electrode 22. The module is configured to analyze the signals and may present the results of the analysis in a standard ECG format, typically a graphical representation moving with time, on screen 48. Module 36 typically also estimates other features of the electropotential signals, such as deriving the LATs of regions contacted by electrode 22.

Probe tracker module 30 tracks sections of probe 24 while the probe is within subject 26. The tracker module typically tracks both the location and orientation of distal end 32 of probe 24, within the heart of subject 26. In some embodiments module 30 tracks other sections of the probe. The tracker module may use any method for tracking probes known in the art. For example, module 30 may operate magnetic field transmitters in the vicinity of the subject, so that magnetic fields from the transmitters interact with tracking coils located in sections of the probe, such as distal end 32, being tracked. The coils interacting with the magnetic fields generate signals which are transmitted to the module, and the module analyzes the signals to determine a location and orientation of the coils. (For simplicity such coils and transmitters are not shown in FIG. 1.) The Carto® system produced by Biosense Webster, of Diamond Bar, Calif., uses such a tracking method. Alternatively or additionally, tracker module 30 may track probe 24 by measuring impedances between electrode 22 and electrodes on the skin of subject 26. (In this case electrode 22 may provide both ECG and tracking signals.) The Carto3® system produced by Biosense Webster uses both magnetic field transmitters and impedance measurements for tracking.

Using tracker module 30 processor 40 is able to measure locations of distal end 32, and form location coordinates of the locations in frame of reference 58 for construction of map 50. The location coordinates are assumed to be stored in map display module 56. In addition, map display module 56 is assumed to store location coordinates of items associated with the procedure being performed on heart 34, such as the coordinates of other catheters used in the procedure, and/or the coordinates of sites within the heart that have been ablated.

User 28 is assumed to perform an ablation procedure on tissue of heart 34, and ablation module 60 controls the ablation energy input to the heart. In addition, the module also monitors the progress of the ablation, and acquires and stores values of parameters of the ablation. For example, assuming that the ablation energy is supplied in the form of electromagnetic radio-frequency (RF) energy, the module records the frequency and the intensity of the RF energy, as well as the duration of time over which the energy is applied to the heart tissue. Other ablation parameters tracked by the ablation module typically include a "goodness of contact" of electrode 22 with the tissue being ablated, an angle made by distal tip 34 with the tissue, a force between the distal tip and the tissue, a rate of irrigation of the tissue, and an indicator of the tissue type.

Other modules in processor 40 measure auxiliary information associated with the ablation procedure. For clarity and simplicity, other modules measuring the auxiliary information, such as the force on the distal tip performing the ablation, the temperature of the tissue being ablated, and the irrigation rate applied to the distal tip, are not shown in FIG. 1.

Figure 2:
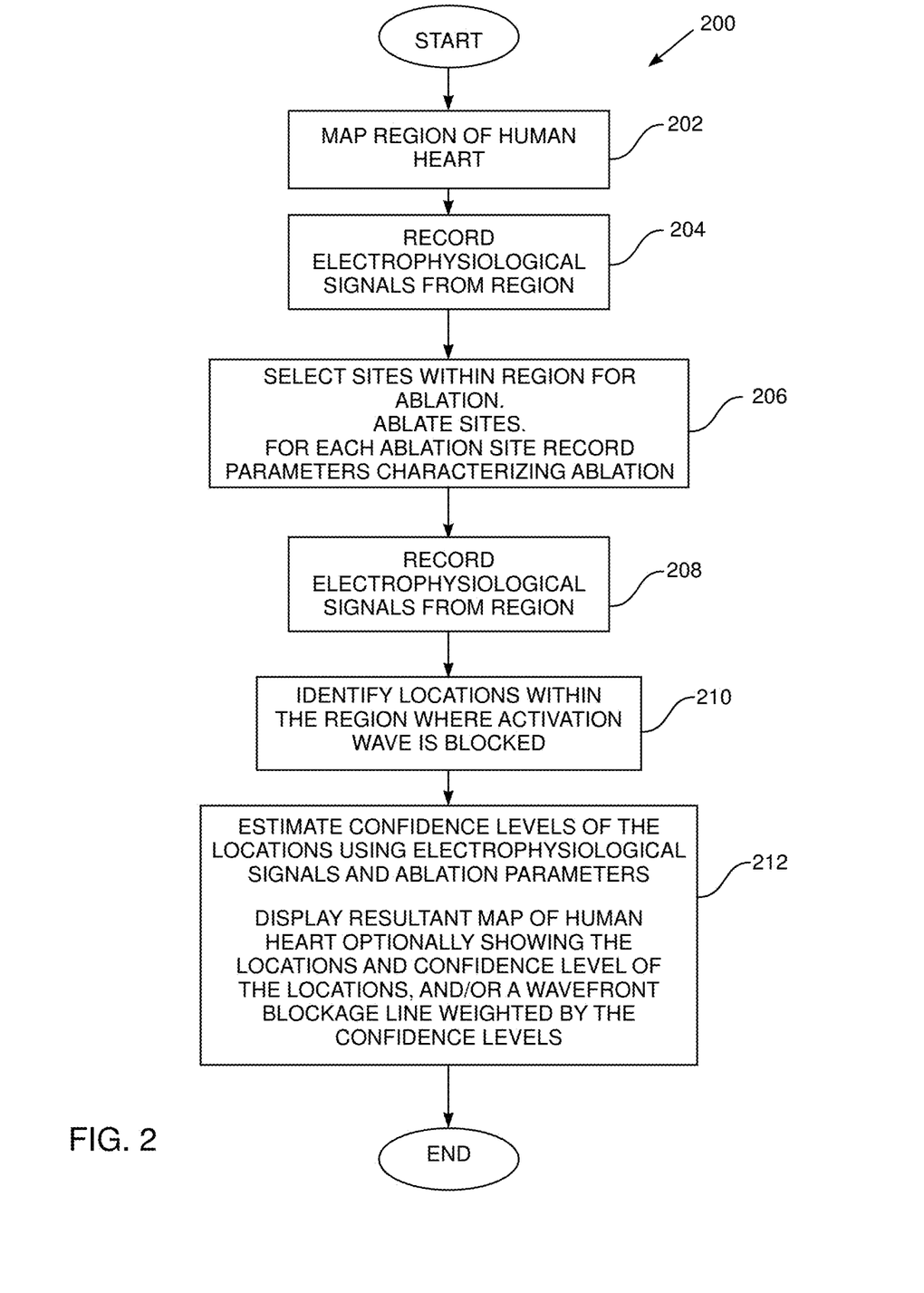
FIG. 2 is a flowchart of steps performed by the system in identifying wavefront blockage locations, according to an embodiment of the present invention.

FIG. 2 is a flowchart 200 of steps performed by system 20 in identifying wavefront blockage locations, and FIGS. 3A-3F are schematic diagrams illustrating steps of the flowchart, according to an embodiment of the present invention. While for simplicity and clarity initial steps of the flowchart are assumed to be performed sequentially, it will be understood that the initial steps may be performed concurrently or even in other orders from that given here.

Figure 3A:
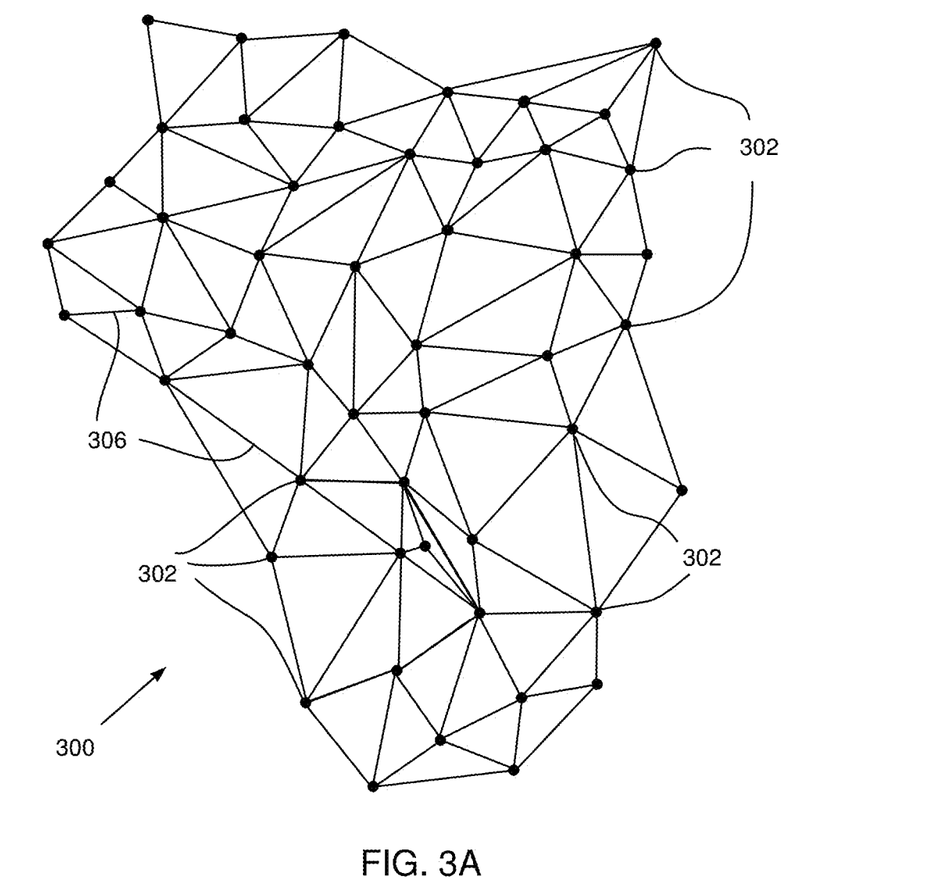
FIGS. 3A-3F are schematic diagrams illustrating steps of the flowchart, according to an embodiment of the present invention.

In a mapping step 202, a map of a desired region 300 of heart 34, such as the interior surface of the left atrium, is generated. The mapping may typically be performed by moving distal end 32 of probe 24 within the region, and recording locations of the distal end as it contacts the surface of the region using tracker module 30. The movement of the distal end generates a multiplicity of point locations of the surface, the coordinates of which are stored by the tracker module. FIG. 3A schematically illustrates locations 302 that have been acquired by the tracker module.

Processing unit 42 uses locations 302 to generate a surface map of the desired region of the heart, typically by initially forming a mesh of line segments 306 connecting locations 302. The mesh may be formed using any convenient mesh generation method known in the art, such as the Ball-Pivoting Algorithm. Once the mesh has been formed, the processing unit may generate the surface map by interpolating between locations 300 and line segments 306, and map display module 56 may be used to display a representation of the surface map of the desired region on screen 48.

Figure 3B:
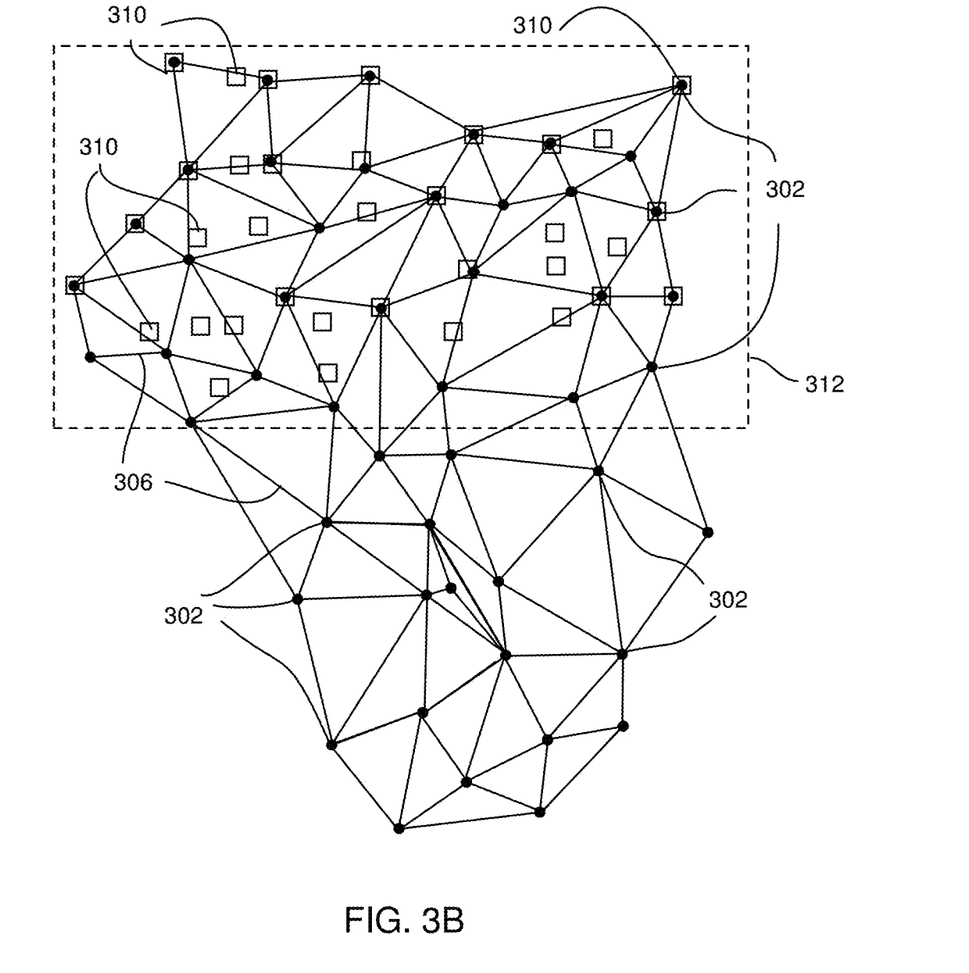

In an initial electrophysiological signal step 204, electrode 22 together with ECG module 36 is used to record electric potentials at positions 310, (illustrated in FIG. 3B) within region 300. While positions 310 are generally situated over the whole of region 300, for simplicity only positions 310 within a dashed rectangle 312 are shown in FIG. 3B. Typically, at least some positions 310 coincide spatially and/or temporally with locations 302, since the mapping of step 202 and the signal recording of step 204 may be performed simultaneously. However, there is no requirement of such a coincidence, as the mapping and the recording may be performed separately.

At each position 310 the potential is recorded over a period of time, typically a number of heart beats, so that the signal for a specific position comprises a set of voltage-time pairs. Processing unit 42 and module 36 may use the recorded signals to generate electrocardiograph (ECG) graphs of the signals for each position 310, and the graphs may be displayed on screen 48. In addition, the processing unit and the module may analyze the signals to derive parameters related to the operation of heart 34, such as a local activation time (LAT) at the location.

Figure 3C:
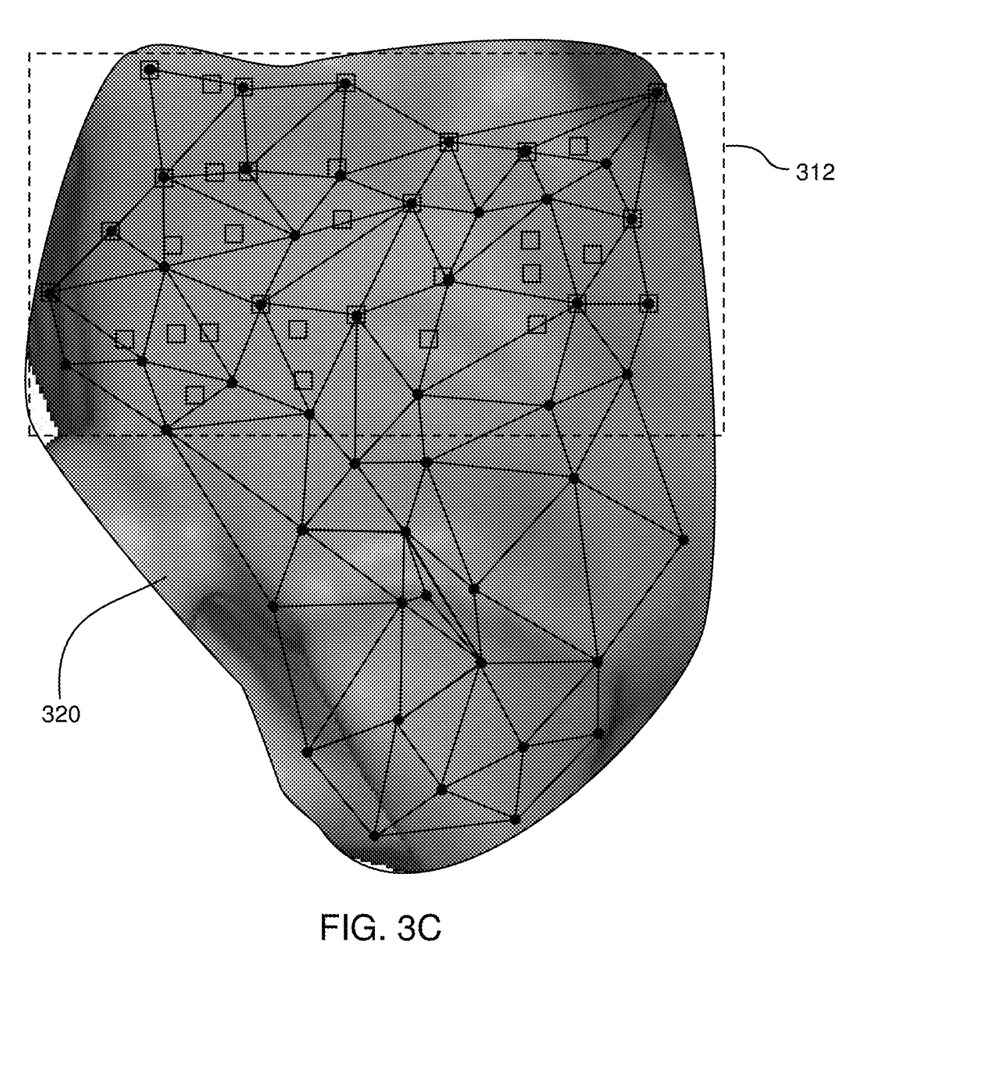

The processing unit may overlay the derived parameters onto the map of step 202, and present the result in the form of an intermediate 3D electrophysiological surface map 320 on screen 48. FIG. 3C illustrates surface map 320, including underlying elements of the mesh formed in step 202. Typically the intermediate 3D map illustrates values of the derived parameters according to a color scale, so that the map is presented as a surface, with colors applied to regions of the surface corresponding to the value of the derived parameters of the regions. FIG. 3C schematically shows the colors of surface map as different gray scales.

Inspection of intermediate surface map 320 enables user 28 to make a preliminary identification of regions of the surface where there appears to be atypical behavior of the derived parameters. For example, for a subject with atrial fibrillation, the map may indicate the presence of one or more re-entrant arrhythmias in a heart chamber that is being inspected. This is an example where the wavefront of the electrical signal in the heart progresses in an abnormal fashion, and other examples of abnormal wavefront progression will be apparent to those having ordinary skill in the art.

Figure 3D:
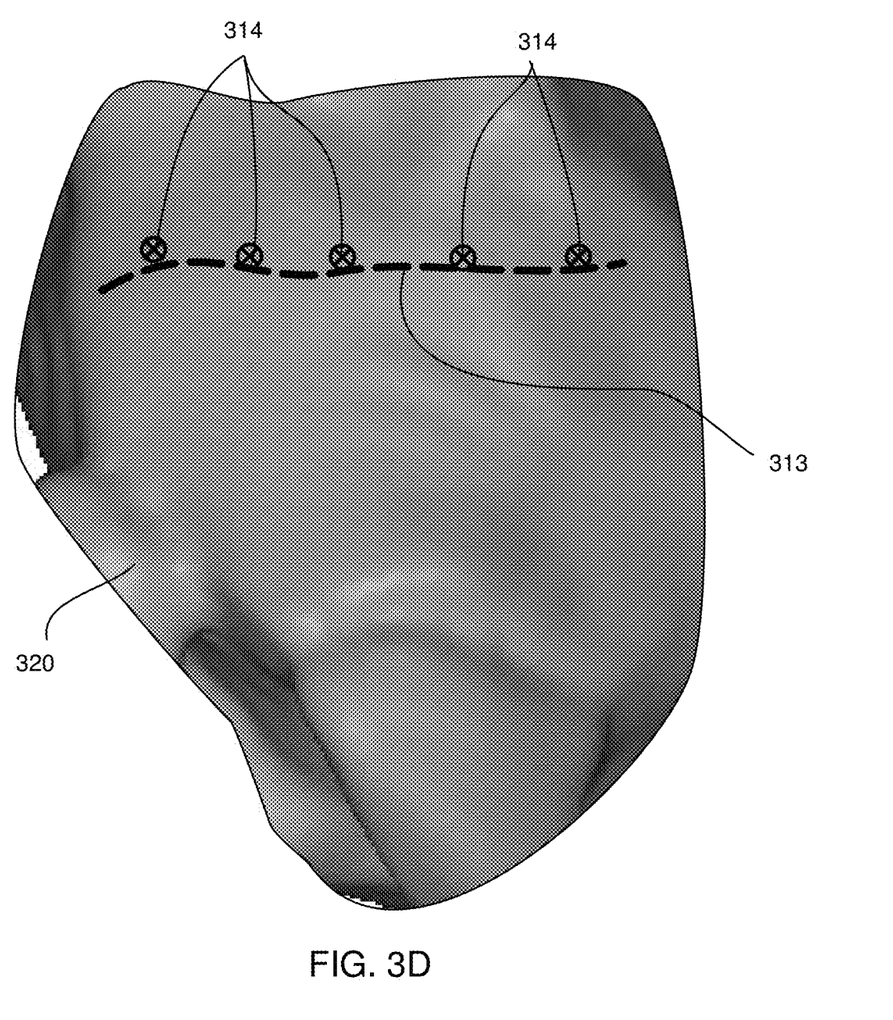

In an ablation step 206, typically performed after the inspection of the intermediate map described above, user 28 selects sites within heart 34 which are to be ablated. The ablation of the sites is to correct the atypical behavior observed in the intermediate map inspection, by blocking any abnormal progression of the wavefront at the ablated sites. FIG. 3D schematically illustrates a line 313, plotted on intermediate map 320, corresponding to an abnormal wavefront.

User 28 performs the ablation at each of the selected sites, and as the ablation is performed, the processing unit uses the ablation module to record parameters characterizing a quality of the ablation. FIG. 3D schematically illustrates locations 314 of ablation sites, plotted on intermediate map 320.

The characterizing parameters recorded by the processing unit typically include at least some of:
A power applied during the ablation
A length of time of the ablation
A force magnitude of the distal end on the tissue being ablated
An angle of contact between the distal end and the tissue while ablation is performed
An estimate of a "goodness of contact" between the distal end and the tissue during the ablation
A temperature and/or a temperature distribution of the tissue being ablated
A rate of irrigation of the tissue In some embodiments the characterizing parameters of the quality of the ablation include an assessment of the quality using images of the sites from a modality other than the RF ablation modality of system 20, such as magnetic resonance imaging (MRI) images and/or ultrasound images. The assessment may be made by user 28, and provided to the processing unit using images which are typically generated after the ablation (described above) has been performed.

Figure 3E:
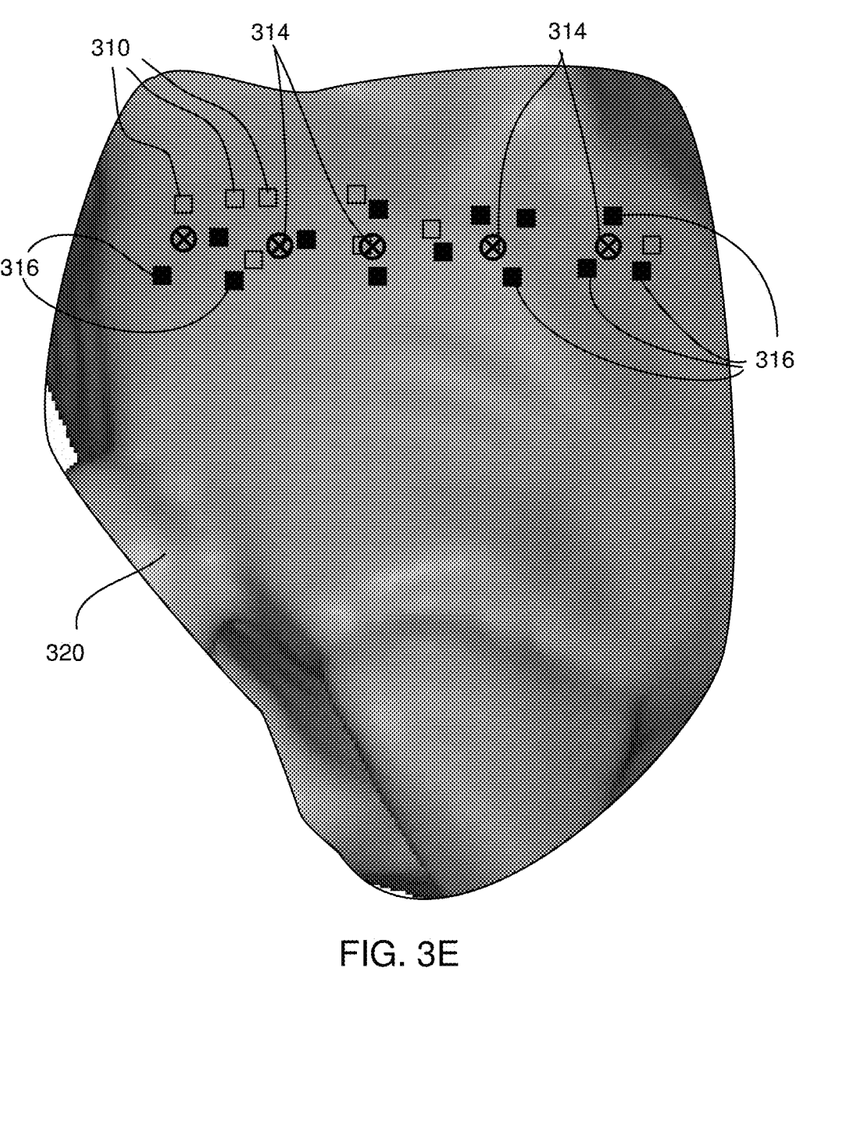

In a subsequent electrophysiological signal step 208, user 28 repeats the recording of electropotentials within region 300, substantially as described above for step 204, by measuring electrical signals within the region. The repeat of the recording may be made at some or all of locations 310, or alternatively or additionally at different locations 316. Typically, at least some of locations 310 or 316 are selected to be in proximity to the ablation site locations 314. FIG. 3E schematically illustrates locations 316 and locations 310 wherein electropotentials are recorded in step 208.

In a wave blocking location step 210, processing unit 42 identifies locations within the region where the activation wave of electropotentials is expected to be blocked. Typically, the identified locations correspond to ablation site locations 314 of step 206, and/or locations in the vicinity of line 313 of step 206.

In a mapping preparation step 212, the processing unit prepares a map showing locations identified in step 210 as expected blocking sites, herein assumed to correspond to ablation site locations 314. In addition, the processing unit calculates a confidence level for each identified site, where the confidence level is a measure of a quality of wavefront blocking.

The confidence level is calculated according to the ablation characterizing parameters recorded in ablation step 206. For example, the confidence level increases as the ablation power increases, and also increases as the length of ablation time increases. Furthermore, the confidence level typically also increases as any of the force magnitude, the "goodness of contact," or the tissue temperature increase. A numerical value of the confidence level may be estimated for each of these ablation parameters, as well as for others such as the angle of contact and the rate of irrigation, from previously acquired ablation data, and/or by calibration experiments that may be performed before operation of system 20. Such calibration experiments do not require undue experimentation by user 28.

The electrophysiological signals recorded in step 208 and/or in step 204 may also be used to assess the confidence level. For example, if, in proximity to a given ablation location 314, an amplitude of the signal recorded in step 208 is lower than that recorded in step 204, then the confidence level of the given site as blocking the wavefront formed may be considered to be higher than if the amplitudes are approximately the same.

In an embodiment of the present invention, processing unit 42 combines the two confidence levels referred to above, i.e., the level derived from the ablation characterizing parameters and the level derived from the electrophysiological signals, so as to estimate an overall confidence level. Thus, for each wave blocking location identified in step 210, the processing unit assigns an overall confidence level that is an overall measure of the quality of the wavefront blocking of the site, and that is an estimate of the quality of the ablation performed at the site.

Figure 3F:
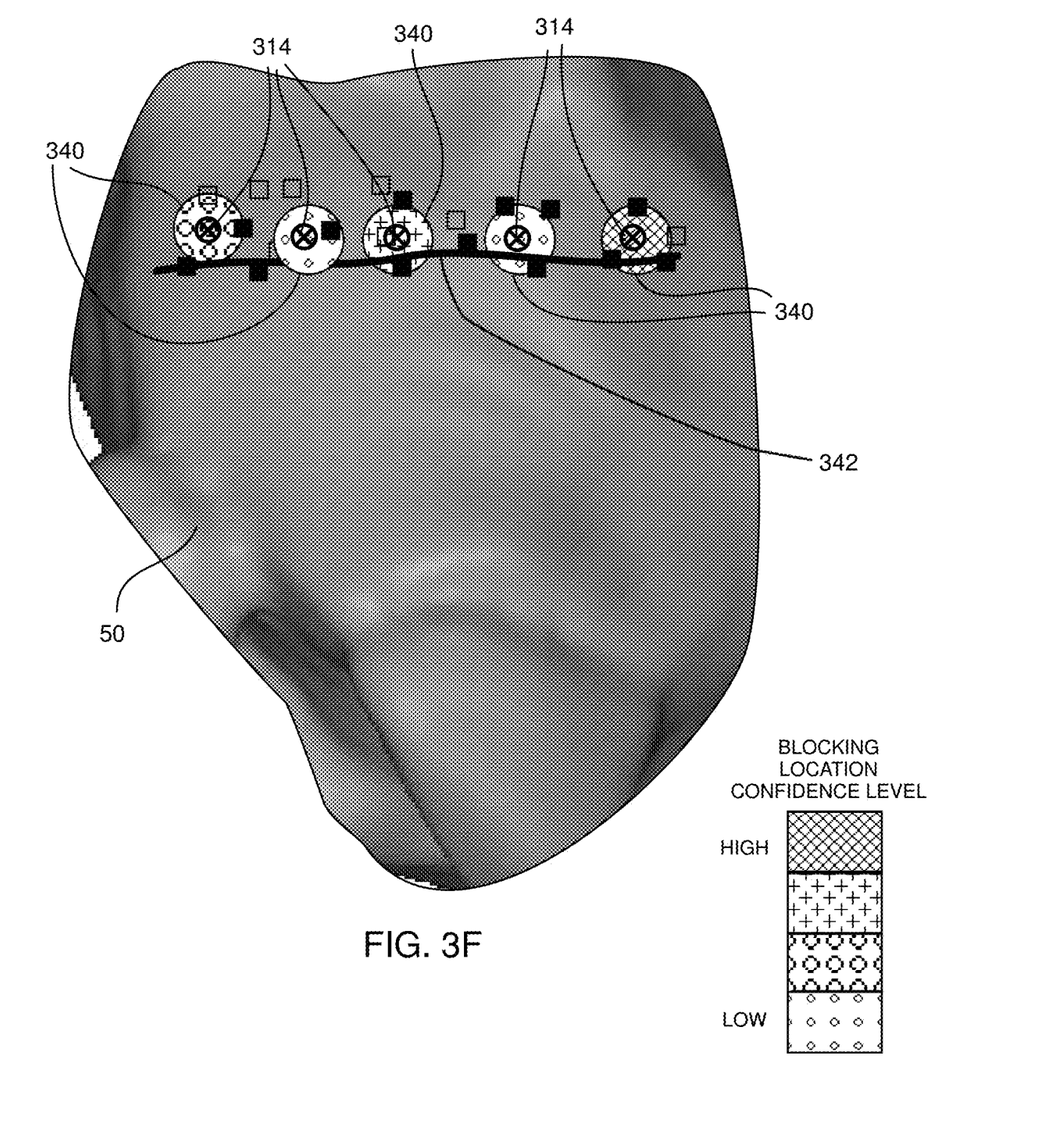

In some embodiments the processing unit displays the prepared map on screen 48 (FIG. 1) as resultant map 50, including in the resultant map locations of wavefront blockages, together with an indication 340 in the resultant map of the overall confidence level of each location, as is illustrated in FIG. 3F. The indication may be by any convenient method known in the art, such as changing a color and/or a size and/or a shape of a symbol of a given location according to its confidence level. Alternatively or additionally, the indication may be incorporated into software generating the map, and user 48 may view the confidence level, typically by moving a cursor over the symbol of the location, using operating controls 38. Further alternatively or additionally, the overall confidence level indication may be included in the map as a colored and/or shaded region in proximity to the wavefront blockage location. FIG. 3F illustrates the different confidence levels by different shadings within a region surrounding the blocking location.

In some embodiments, a line 342 may be displayed on map 50, the line illustrating blockage of the wavefront in the vicinity of locations 314. Line 342 is based on line 313 (FIG. 3D), but the path of line 342 has been weighted by the confidence levels.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A computer implemented method, comprising:
   before an ablation step, recording a first set of electrophysiological signals at a plurality of first locations in a region of a human heart;
   during an ablation step, recording parameters indicative of a quality of ablation performed at one or more ablation sites in the region of the human heart;
   after the ablation step, recording a second set of electrophysiological signals indicative of a wave of electrical activation flowing through the region at a plurality of second locations in the region of the human heart;
   identifying from a comparison of the first set of electrophysiological signals and the second set of electrophysiological signals a plurality of blocking locations within the region at which the wave is blocked from flowing by the ablation during the ablation step;
   for each identified blocking location of the plurality of blocking locations within the region of the heart:
      estimating a first confidence level with respect to a blockage of the wave at the identified blocking location by comparing an electrophysiological signal from the second set of the electrophysiological signals with an electrophysiological signal of the first set of the electrophysiological signals, where the electrophysiological signals from the first set of electrophysiological signals and the second sets of electrophysiological signals are recorded over a plurality of heart beats in proximity to the identified blocking location;
      estimating a second confidence level with respect to the blockage of the wave at the identified blocking location in response to the recorded parameters indicative of a quality of ablation; and
      determining an overall confidence level for each blocking location by combining the first confidence level and the second confidence level, the overall confidence level being an overall measure of the quality of the wave blocking and the ablation of the identified blocking location;
      displaying a map of the human heart including an identified blocking location and an indication of the overall confidence level of that blocking location; and
   wherein the first set of electrophysiological signals and the second set of electrophysiological signals are unstimulated electrophysiological signals from the human heart; and
   wherein the method further comprises increasing a given confidence level at a given identified blocking location if an amplitude of an electrophysiological signal in proximity to the identified blocking location in the second set of electrophysiological signals is lower than an amplitude of an electrophysiological signal in the first set of electrophysiological signals.

2. The method according to claim 1, wherein the recorded parameters comprise one or more of a power applied during the ablation, a length of time of the ablation, a force magnitude on a probe applying the ablation, and a temperature of tissue undergoing the ablation.

3. The method according to claim 2, and wherein increasing the confidence levels as at least one of the power, the length of time, the force magnitude, and the temperature increases.

4. The method according to claim 1, wherein identifying the blocking locations comprises inspecting an electrophysiological surface map generated in response to the first set of electrophysiological signals and the second set of electrophysiological signals.

5. The method according to claim 4, wherein the electrophysiological surface map is configured to provide an indication of a re-entrant arrhythmia.

6. The method according to claim 1, wherein the recorded parameters provide an assessment of the quality of the ablation based on at least one of a magnetic resonance imaging (MRI) image and an ultrasound image of the one or more ablation sites.

7. An apparatus, comprising:
a screen; and
a processor communicating with a memory and the screen, the processor configured to;
before an ablation step, record a first set of electrophysiological signals at a plurality of first locations in a region of a human heart;
during the ablation step, record parameters indicative of a quality of ablation performed at one or more ablation sites in the region of the human heart,
after the ablation step, record a second set of electrophysiological signals indicative of a wave of electrical activation flowing through the region at a plurality of second locations in the region of the human heart,
identify from a comparison of the first set of electrophysiological signals and the second set of electrophysiological signals a plurality of blocking locations within the region at which the wave is expected to be blocked from flowing by the ablation performed during the ablation step,
for each identified blocking location within the region of the heart:
estimate a first confidence level with respect to a blockage of the wave at the site by comparing an electrophysiological signal from the second set of electrophysiological signals with an electrophysiological signal in the first set of electrophysiological signals, where the electrophysiological signal from the first set and the electrophysiological signal from second set are recorded over a plurality of heart beats in proximity to the identified blocking location;
estimate a second confidence level with respect to the blockage of the wave at the identified blocking location in response to the recorded parameters indicative of a quality of ablation; and
determine an overall confidence level for each identified blocking location by combining the first confidence level and the second confidence level, the overall confidence level being an overall measure of the quality of the wave blocking of the ablation performed at the identified blocking location; and
display a map of the human heart including the identified blocking location and an indication of the overall confidence level of that identified blocking location on the screen;
wherein the first set of electrophysiological signals and the second set of electrophysiological signals are unstimulated electrophysiological signals from the human heart; and
wherein the processor is further configured to increase a given confidence level at a given blocking location if an amplitude of an electrophysiological signal in proximity to an identified blocking location in the second set of electrophysiological signals is lower than an amplitude of an electrophysiological signal in the first set of electrophysiological signals.

8. The apparatus according to claim 7, wherein the parameters comprise one or more of a power applied during the ablation, a length of time of the ablation, a force magnitude on a probe applying the ablation, and a temperature of tissue undergoing the ablation.

9. The apparatus according to claim 8, and wherein increasing the confidence levels as at least one of the power, the length of time, the force magnitude, and the temperature increases.

10. The apparatus according to claim 7, wherein the identified blocking locations are derived by inspecting an electrophysiological surface map generated in response to the first set of electrophysiological signals and the second set of electrophysiological signals.

11. The apparatus according to claim 10, wherein the electrophysiological surface map is configured to provide an indication of a re-entrant arrhythmia.

12. The apparatus according to claim 7, and comprising a probe configured to acquire the first set of electrophysiological signals and the second set of electrophysiological signals and to convey the first set of electrophysiological signals and the second set of electrophysiological signals to the processor.

13. The apparatus according to claim 7, wherein the recorded parameters comprise an assessment of the quality of the ablation, the assessment being based on at least one of a magnetic resonance imaging (MRI) image and an ultrasound image of the one or more ablation sites.

14. The method according to claim 1, wherein displaying the map comprises displaying a line illustrating a path where the wave is blocked from flowing, and wherein the path is weighted by the overall confidence levels.

15. The apparatus according to claim 7, wherein displaying the map comprises displaying a line illustrating a path where the wave is blocked from flowing, and wherein the path is weighted by the overall confidence levels.

* * * * *